US005525509A

United States Patent [19]

Christner et al.

[11] Patent Number: 5,525,509

[45] Date of Patent: Jun. 11, 1996

[54] METHOD FOR THE ENZYMATIC LIMING OF SKINS AND HIDES

[75] Inventors: Juergen Christner; Tilman Taeger, both of Seeheim-Jugenheim; Gertrud Wick, Darmstadt, all of Germany

[73] Assignee: Röhm GmbH, Darmstadt, Germany

[21] Appl. No.: 311,717

[22] Filed: Sep. 23, 1994

Related U.S. Application Data

[63] Continuation of Ser. No. 949,537, Nov. 9, 1992, abandoned.

[30] Foreign Application Priority Data

Mar. 26, 1991 [DE] Germany .......................... 41 09 826.9

[51] Int. Cl.[6] .............................. C14C 1/00; C14C 1/06; C12N 9/20

[52] U.S. Cl. .......................... 435/265; 435/198; 8/94.18; 8/150.5

[58] Field of Search .................................... 435/265, 198; 8/94.1 R, 94.15, 94.16, 94.18, 150.5; 162/2; 424/94.6; 252/8.57

[56] References Cited

U.S. PATENT DOCUMENTS

| | | | |
|---|---|---|---|
| 4,273,876 | 6/1981 | Monsheimer | 435/265 |
| 4,960,428 | 10/1990 | Christner et al. | 8/94.18 |
| 5,082,585 | 1/1992 | Hessel et al. | 252/174.12 |
| 5,089,414 | 5/1990 | Christer et al. | 435/265 |

FOREIGN PATENT DOCUMENTS

| | | |
|---|---|---|
| 11656/88 | 8/1988 | Australia . |
| 0469758 | 5/1914 | France . |
| 2856320 | 7/1980 | Germany . |
| 2233665 | 1/1991 | United Kingdom . |

OTHER PUBLICATIONS

Christner. CA 118:24082. Abstract of EP 505920 Sep. 30, 1992.
Hu et al, "Use of Alkalene Lipose for Degrading of Pigskin Leather" Chinese Article 1982 (Full Text of Reference 5).
Hu et al, "Use of Alkaline Lipose for Degreasing of Pigskin Leather" Translation of Chinese Article (Ref. 55) 1982.
Christner, J. "The Use of Lipases in the Beamhouse Processes", JALCA, vol. 87 (1992) pp. 128–40.
Zhang et al. "Test Use of Alkaline Lipase in Degreasing Pigskin". CA98 (14):109245h 1982.
Hu et al. "Use of Alkaline Lipase for Degreasing of Pigskin Leather". CA99(18):141865s. 1983.
Yugaguku et al., unidentified source 23(2) (1974), pp. 1–10 "Influence of Surface Active Agents on Detergent Tolerance of Lipases".
Jensen et al., "Lipolase. A Microbial Lipase etc.", Comun. Jorn. Com. Esp. Deterg., 21, 1990 pp. 23–27.
"Enzymatic Degreasing etc.", Novo Nordisk Application Sheet, Nov. 1990.
Kirk–Othmer, Encyc. of Chemical Technology, 3d ed., vol. 9, (1990) pp. 190 and 192.
Ullmann, Encyc. of Industrial Chemistry, 5th ed, vol. A9 (1987) pp. 395 and 397.
Yeshoda et al., Leather Science (Madras) 25(2) (1978) pp. 77–86.
Wood, "The Puering, Bating & Drenching of Skins", Spon, Ltd., London (1912), pp. 137 and 141.
Bienkiewicz, "Physical Chemistry of Leather Making", Krieger Publ. Co., Malabar, Fla. (1983) p. 226.
Leather Technician'a Handbook, Leather Producers' Assn., (1971) pp. 93–95.
Kirk–Othmer. Ency. of Chemical Technology, 3rd ed. vol. 14 (1990) pp 209, lines 40–41.
Ullmann, Ency. of Industrial Chemistry, 5th ed. vol. A9 (1987) p. 414.
"The Chemistry and Technology of Leather", vol. III, Reinhold, New York (1962), pp. 186–191.
"The Chemistry and Technology of Leather", vol. 1, Krieger Publ. Co. Huntington, New York, (1978) p. 359.
Thorstensen, "Practical Leather Technology", Van Nostrand Reinhold, New York (1969) Chapters 6 and 7 pp. 82–110.
Lamb, "The Manufacture of Chrome Leather", Anglo–American Tech. Co. Ltd., London (1923) pp. 33–39 and 105–116.
Catalog of the Sigma Company (1994), p. 627.
Posorske, "Industrial Scale Application of Enzymes etc.", J. Amer. Oil Chem. Soc. 61(11) (1984) pp. 1758–1760.
"Pancreatic Trypsin Novo", product sheets, Novo Nordisk, Feb. 1990 and Aug. 1990.
"Novo Enzymes for the Tanning Industry", information sheet, Novo Nordisk (1972) pp. 2–7 and appendices.
Kirk–Othmer Ency. of Chemical Technology, 3rd ed. vol. 22 (1990) p. 390.
"Novo Enzymes", product sheet for lipolase™ of Novo Industri A/S, Dec. 1987.
Kirk–Othmer Encyclopedia of Chemical Technology, 3rd Ed., vol. 8, Wiley & Sons, New York, 1979, pp. 910–916.
Leather Technical Glossary in Six Language, Eduard Roether Verlag, Darmstadt, Germany, p. 186.
Kirk–Othmer, op. cit., 3rd Ed., vol. 9, pp. 190, 202, 216 (1990).
The Merck Index, 9th Edition, Editor Windholz, Merck & Co., Rahway, N.J. 1976, p. 908.
Chemical Abstract, 82 113205g (1975).
Kirk–Othmer, op. cit., 3rd Ed., vol. 5, p. 362 (1990).
Biotechnology, Rehm and Reed, Editors, vol. 7a "Enzyme Technology" J. Kennedy, Editor, VCH, Weinheim, Germany, p .644 (1987).
Kirk–Othmer, op.cit. 3rd Ed., vol. 14, pp. 208, 209 (1981).
Chemical Abstracts Registery 9001–92–73 "Proteinase" (1993).
Chemical Abstracts 97, 57467q (1982).

*Primary Examiner*—Jeanette Hunter
*Assistant Examiner*—T. J. Reardon

[57] ABSTRACT

A method for preparing unhaired hides ready for tanning from hides and skins using proteolytic and lipolytic enzymes in the beamhouse, whereby in at least one of the partial steps of the beamhouse consisting of a) liming in the pH range 11.5–14 and b) bating in the pH range 5–11.5, alkaline lipases (E.C.3.1.3.) having an activity optimum in the pH range 9–11 are added to the aqueous floats corresponding to these partial steps.

6 Claims, No Drawings

METHOD FOR THE ENZYMATIC LIMING OF SKINS AND HIDES

This application is a continuation of application No. 07/949,537 filed Nov. 9, 1992 and now abandoned.

FIELD OF THE INVENTION

The invention relates to enzymatically supported liming and bating processes wherein alkaline lipases are used, preferably in combination with proteolytic enzymes.

DESCRIPTION OF THE RELATED ART

The planned use of enzymes in leather preparation began with the introduction of the enzymatic bate by Dr. Otto R öhm in 1907 (DE-PS 200 519). From this time forward—against a background of increasing ecological knowledge —, the use of proteases in different partial operations in the beamhouse has been proposed and also realized in practice (cf. E. Pfleiderer and R. Reiner in Biotechnology, editor H.-J. Rehm, pp 729–743, VCH 1988). Also amylases, particularly in combination with proteases, have similarly found an entry into the bating operation of the beamhouse (U.S. Pat. No. 4,273,876). The concurrent use of lipases and amylases (in the form of pancreatin) in the presence of desoxycholic acid is known from Hungarian Patent 3325 (Chem. Abstr. 77, 7341k). The use of lipases for the degreasing of skins and hides, particularly of pigskins and sheepskins having a high fat content, and of scraps, occurs according to nature. To be sure there are recommendations for their use for degreasing [e.g. L. H. Posorske, J. Am Oil Chem. Soc. 61 (11) 1758–1760 (1984); K. Yeshodha et al., Leather Sci. (Madras) 25 (2) 77–86 (1978), Chem Abstr. 89, 199097; T. Nielsen, Fette, Seifen, Anstrichm. 87 (1) 15–19 (1985)], as well as negative experiences, e.g. with respect to pickled and delimed unhaired sheepskins [cf. A Vulliermet et al., Technicuir 16 (4) 64–76 (1982), Chem. Abstr. 97, 57467q; Chem. Abstr. 82, 113205g]. In the last mentioned literature source, an enzymatic decomposition of fat with lipases or enzyme preparations containing lipase in a pH region below 8, preferably in a moderately acid pH range, is considered.

In Biotechnology., editor H.-J. Rehm, vol. 7a, loc.cit. p.644, it is remarked that microbial and pancreatic lipases (E.C.3.1.1.3) cannot be used as enzymes for washing agents because of their notorious instability under alkaline conditions, quite apart from their price. The decomposing effect of proteases toward proteins, which is what lipases are, teaches away from a concurrent use of lipases and proteases.

Recently, an enzymatically supported soaking method for hides and skins has been recommended, in which the soaking floats contain A) lipases having an activity optimum in the pH region from 9 to 11, B) proteases having activity in the pH region from 9–11, and C) surface active agents, wherein the pH value of the soaking float is in the region from 9 to 11 (cf. German patent application P 39 22 748.0corresponding to U.S. Pat. No. 5,089,414 granted Feb. 18, 1992). For this, enzymes obtained from Aspergillus species and from certain special genetically altered strains have been found to be especially suitable, for example an alkaline lipase obtained by recombination from an *Aspergillus oryzea* strain, having a pronounced activity optimum between pH 9 and 11, as well as a lipase commercially available under the trademark "LIPOLASE 100 T" (Novo Industri A/S, Bagsvaerd, 2880 Denmark). Those skilled in the art know from U.S. Pat. No. 5,082,585 to Hessel et al. granted Jan. 31, 1992, i.e. before the filing of the present application, that this enzyme is obtained by cloning the gens from *Humicola lanuginosa* and expressing this gene in *Aspergillus oryzae*. LIPOLASE is a 1,3-specific, recombinant fungal lipase. Its molecular weight by SDS-PAGE is about 35 kD and the pI for this enzyme is about 4.4. The pH optimum, as measured at 30° C. on tributyrin, is 9–11. LIPOLASE is a glycoprotein.

Problem and solution

In any event, the working up of raw goods which are very rich in fat (such as pigskins, sheepskins, scraps, etc.) presents difficult problems to one preparing leather. These problems can be arranged under the captions: insufficient liming and freedom of the unhaired hides from scud after opening of the hide structure, as well as the formation of disruptive calcium soaps, which can lead to unpleasant smears on the skins.

Also, the bating of fatty unhaired hides presents difficulties because an adherent fatty surface film hinders penetration of the bating enzymes and can counteract the optimum loosening of scud.

The teaching of aforementioned German patent application P 39 22 748.0 does not extend beyond the use of certain lipases in soaking, i.e. in a pH region of 9–11. Since, according to the instructions of their manufacturers, these enzymes have their pH optimum in the range from 10–11, it appears that the use recommendation according to the aforementioned German patent application is in a region which would sensibly come under consideration, at least for this parameter. Exceeding this pH region appeared ab initio hardly to promise success; rather, the skilled artisan must reckon with a considerably reduced efficacy and decreased stability, the farther removed he is from the aforementioned region.

SUMMARY OF THE INVENTION

It has now been found that, surprisingly, alkaline lipases (AL), which characteristically have a pH optimum from about 9–11, particularly from 10–11, can advantageously be used in the beamhouse in the aqueous floats appropriate to the steps of a) liming in the pH region from 11.5–14, particularly 12–13.5, and especially from 12–13, and b) bating in the pH region from 5–11.5, particularly 7–9.5, and especially 8–9.

The effect is particularly pronounced if the aforementioned lipases are used in an enzyme combination (EC) together with neutral or alkaline proteases (P) chosen to correspond to the step in question. Preferably, this involves the pertinent proteases used in industry.

DESCRIPTION OF PREFERRED EMBODIMENTS

"Liming" should be understood to refer to the known process for swelling the epidermis and loosening hairs and guard hairs to the point of removal under the influence of alkaline liming chemicals (cf. F. Stather, *Gerberei und Gerbereitechnologie,* pp 166–199, Akademie-Verlag 1967; Ullmann's *Encyclopedia of Industrial Chemistry,* 5th edition, vol. A15, pp 259–282, VCH 1990). Depending on how the process is carried out, the liming can be arranged to retain hair or to destroy it. Liming is generally carried out in the pH region 12–13, either in the form of the so-called "hydroxyl liming", where in particular, calcium hydroxide, as well as alkali metal hydroxides, ammonia, and other hydroxides of alkaline earth metals, are used, or in the form of the so-called sulfide liming, the active components of which are alkali metal sulfides or alkaline earth metal sulfides, optionally in admixture with other basic alkalis or alkaline earth metal alkalis. The liming process of the present invention extensively follows the method of the state of the art [cf. Ullmann's *Encyclopedia of Industrial Chemistry,* 5th edition, vol. 15A, pp 259–282, VCH (1990); Ullmanns *Enzyklopädie der Technischen Chemie,* 4th edition, vol. 16, pp 119–120, Verlag Chemie (1978), 3rd edition, vol. 11, p 609, Urban & Schwarzenburg].

The liming procedure according to the present invention can be performed with a float length of 50–250, preferably 80 to 150, percent of water by weight of the hides.

In general, the liming process requires 12 to 36 hours, particularly 16 to 20 hours.

In the steps of deliming and bating, which follow liming in the beamhouse, the hides and skins are neutralized and enzymatically bated. In this, the hides and skins are first washed and delimed, preferably using weak acids, for example organic acids like lactic acid, formic acid, acetic acid, butyric acid, propionic acid, or dicarboxylic acids inter alia, or using weakly acidic inorganic compounds such as sodium bisulfite, sulfophthalic acid, ammonium sulfate, or even carbon dioxide. In general, attention is paid during deliming that a pH region results which will be favorable for the subsequent addition of enzymes for bating. For pancreatic enzymes, this region is at pH 7.5–8.2. The subsequent bate serves to remove residues of epidermis and hair and to additional opening of the hide structure. As a rule, the enzymatic bating component, especially enzymes of the pancreatic complex, is added after a certain time. Lipases can also belong to the enzymes of the pancreatic complex (DE-A 37 04 465). The region between 32 and 37 C° has proved suitable as the bating temperature. Bating generally takes from 1 to 3 hours.

Preferably, the enzymatic additives, particularly those involving enzyme combinations EC, also contain sequestering agents SM, above all to avoid calcium soaps.

Further, the addition of substances acting as emulsifiers ES has proved to lead to particularly good emulsification of fat. The float length corresponds to that for carrying out liming.

The alkaline lipases AL

The lipases to be used according to the invention are, in agreement with the usual definitions, esterases, which hydrolyze glycerin esters of the fatty acids in aqueous emulsion (E.C. 3.1.1.3). Cleavage of the triglyceride preferably takes place in the 1,3-position. In contrast to the pertinent lipases used according to the state of the art, having a region of use from pH 6–9, the lipases according to the present invention have an pronounced activity optimum (e.g. towards olive oil or tributyrin) between pH 9 and 11. Such alkaline lipases were specially developed for the laundering agent industry. They are of microbiological origin. Potential sources for such strains of microorganisms, which may possibly be genetically altered, are, in particular, fungi and bacteria. Certain alkaline lipases occur, for example, in Pseudomonas strains. Also, *Rhizopus sp., Candida sp., Chromobacterium sp.,* can be considered as producing lipases. Further important lipase producers are *Geotrichium sp., Aspergillus sp., Mucor sp., Penicillium sp., Corynebacterium sp., Propionibacterium sp.,* and *Achromobacter sp.*. Specially named are *Rhizopus arrhizus* and *Rh. oryzae, Candida cyclindracea, Chromobacterium viscosum, Geotrichium candidum, Mucor miehi, Mucor pusillus, Penicillium roqueferti* and *P. cyclopium, Corynebacterium acne, Propionibacterium shermanii, Achromobacter lipolyticum, Aspergillus niger,* especially *Aspergillus oryzae.* Certain genetically altered strains have also been found to be particularly suitable, e.g. an alkaline lipase of an *Aspergillus oryzae* strain obtained by recombination and having an outstanding activity optimum between pH 9 and 11, or a lipase commercially available under the trademark "LIPOLASE TM 30 T" obtained by cloning the gens from *Humicola lanuginosa* and expressing this gens in *Aspergillus oryzae* (Novo Industri A/S, DK 2800 Bagsvaerd, Denmark).

Determination of the activity of lipases is carried out in the usual way with olive oil as the substrate, but also with triacetin and tributyrin. [Cf. M. Sémériva et al., Biochemistry 10, 2143 (1971); *Pharmaceutical Enzymes,* edited by R. Ruyssen and A. Lauwers, 1978, (FIP).] If the fat cleaving activity is expressed in kilo-lipase units (one unit= KLCA), tributyrin is used as a substrate working under the standard conditions at 40 C°. (Cf. M. Sémériva, loc.cit..)

For purposes of the present invention, lipase activity is given in LCA units, measured, however, at pH 9.5. According to the invention, the lipases are so employed that a lipase activity of 100–100,000 LCA, preferably 2,000–4,000 LCA, is present in a float per kg of skins at pH 9.5.

The proteolytic enzymes P

The use in liming of proteases which display a sufficient proteolytic activity in the pH region between 9 and 13 is known. They are neutral (E.C.3.4.24) and, particularly, alkaline proteases (E.C.3.4.21) [cf. Kirk-Othmer, *Encyclopedia of Chemical Technology,* 3rd edition, pp 199–202, J. Wiley 1990; Ullmann's *Encyclopedia of Industrial Chemistry, vol. A*9, pp 409–414, VCH 1987; L. Keay, in Process Biochemistry, 17–21 (1971).] In detail, these are.

Alkaline proteases which display their activity optimum approximately in the region pH 8.5–13. These include alkaline bacterial proteases, which for the most part are of the serine type, and alkaline fungal proteases. Named are, above all, the proteases from Bacillus strains such as *B.subtilis, B. licheniformis, B. firmus, B. alcalophilus, B. polymixa, B. mesentericus,* as well as Streptomyces strains like *S. alcalophilus.* The most favorable operating temperature with alkaline bacterial proteases is in general at 40°–60 C° and with fungal proteases at 20°–40 C° . As alkaline fungal proteases are mentioned those from Aspergillus strains, such as *A. oryzae,* from Penicillin strains such as *P.cyanofulvum,* or from *Paecilomces persicinus, inter alia.* The activity of the alkaline fungal proteases is primarily in the pH region 8.0–11.0. As a rule of thumb, one can proceed from an enzyme activity which is between 8,000 and 10,000 L öhlein-Volhard Units (LVU) per gram of enzyme.

Neutral proteases having an activity optimum in the region from pH 6.0–9.0. To this belong, especially, neutral bacterial proteases, which as a rule belong to the metallo enzymes, and fungal proteases, for example neutral Bacillus proteases such as *B. subtilis, B. natto,* and *B. polymixa,* Pseudomonas proteases, Streptomyces proteases, Aspergillus proteases from *A. oryzae, A. parasiticus,* and *Penicillium glaucum.* Neutral bacterial proteases display their optimum activity at operating temperatures of 20–50 C° ., whereas the most favorable operating temperatures for neutral fungal proteases is at 35–40 C°.

The proteolytic activity of the enzymes is usually determined according to the Anson hemoglobin method [M. L.

Anson, J. Gen. Physiol, 22, 79 (1939)] or according to the Löhlein Volhard method [modified by TEGEWA in Leder, 22, 121–126 (1971)]. According to the latter, one Löhlein Volhard Unit (LVU) is that amount of enzyme which, in 20 ml of casein filtrate, causes an increase of hydrolysis product corresponding to an equivalent of 5.75 ($10^{-3}$) ml of 0.1 N NaOH under the test conditions (1 hour, 37 C°). The protease activity in general is between 1,000 and 60,000 LVU per kg of hides, preferably between 2,000 and 14,000 LVU per kg of hides.

Depending on activity, amounts of protease between 0.05 and 0.8 percent, or as a rule of thumb about 0.1–0.25 percent, by weight of the hides and skins are sufficient according to the invention.

As (synthetic) surface active substances, the usual emulsifiers, for example, can be used, particularly those. suitable for the emulsification of fat in water. (Cf. GB-PS 586,540, DE-PS 894,142, FR-PS 899,983, FR-PS 918,523). First of all, non-ionogenic emulsifiers are suitable, for example of the following kinds:

| | | |
|---|---|---|
| I. Polyglycol derivatives (exemplary commercial products given in parentheses) | | |
| α) | fatty acid polyglycols | ("EMULPHOR") |
| β) | fatty alcohol polyglycol ethers | ("DEHYDOL") |
| γ) | alkylphenol polyglycol ethers | ("EMULGIN 286", "FLUIDOL W 100", "MARLOPHEN", "IGEPAL") |
| δ) | fatty acid ethanolamido polyglycol ethers | ("C", "FORYL KW", "EMULGIN") |
| II. Glycerin derivatives | | |
| α) | fatty acid monoglycerides | ("TEGOMOLS) |
| β) | fatty acid polyglycerin esters. | |

Further anionic emulsifiers are, for example, of the following kinds:

| | | |
|---|---|---|
| III. Sulfates $R-OSO_3Na$ | | |
| α) | fatty alcohol sulfates, primary and secondary | ("EPPOL DL conc.", "PERAMIT ML", "TEEPOL") |
| β | fatty alcohol ether sulfates | ("TEXAPON Q") |
| γ) | monoglyceride sulfates | ("VEL") |
| δ) | sulfation products of unsaturated oils and fatty acids | ("LEDEROLINOR DKMS") |
| IV. Sulfonates $RSO_3Na$ | | |
| α) | alkylbenzene sulfonates (ABS,TPS) | ("MARLOPON", "MARLON") |
| β) | alkyl sulfonates | ("MERSOLAT") |
| γ) | fatty acid condensation products | ("IGEPONA", "IGEPONT") |
| δ) | petroleum sulfonates | (contained in: "GRASSAN B") |
| ε) | sulfitation products of unsaturated fatty oils and fatty acids | ("CUTISAN BS") |
| ζ) | short chain alkylbenzene sulfonates, e.g. of cumene, toluene, or xylene. | |

Cationic emulsifiers, e.g. of the following types, are less advantageous:

| | | |
|---|---|---|
| V. Amine salts $RNR_1R_2Hx$ | | ("SAPAMIN", "SOROMIN") |
| VI. Quaternary Ammonium Salts $RNR_1R_2R_3{}^+X^-$ | | ("REPELLAT") |
| α) | ammonium salts | |
| β) | pyridinium salts, | |

wherein the radical R is a long chain alkyl radical having 8–24 carbon atoms, the radicals $R_1$, $R_2$, or $R_3$ as a rule represent short chain alkyl radicals having up to 6 C-atoms.

The emulsifiers usable according to the invention have an HLB value (O/W emulsion) of 8–18, preferably 9–15, especially 12–15. (Cf. Ullmanns *Encyklopädie der Technischen Chemie,* 4th edition, vol. 19.) Combinations of emulsifiers can also advantageously be used., particularly of nonionic and anionic emulsifiers. Emulsifier combinations ES of the following kinds are specially mentioned (EO= degree of ethoxylation):

x% $C_{11}$–$C_{13}$ fatty alcohols ethoxylates having 6–10 EO preferably 8–9 EO y% $C_{15}$–$C_{17}$ paraffin sulfonate—Na salt z% $C_{16}$–$C_{18}$ fatty alcohol amine ethoxylate having 5–7 moles of ethylene oxide, quaternized water to 100%, wherein x=10–50 percent by weight
y=10–50 percent by weight
z=1–10 percent by weight.

The content of emulsifiers in the floats is—depending on the kind—as a rule from 0.1 to 1 percent of the salted weight or green weight of the skins or hides. Remarkably, the precipitates which are to be expected with the above composition do not occur using the preferred combinations. Also, the floats can still contain known sequestering agents. The sequestering agents are chosen from the group formed by the polyphosphates, the phosphonates, the polycarboxylates, ethylenediaminetetraacetic acid (EDTA); nitrilotriacetic acid, diethylenetriaminopentaacetic acid. The content of sequestering agents in the soak float can be from 0 to 0.5 percent by weight, preferably 0.05 to 0.15 percent by weight. (Cf. Kirk-Othmer, *Encyclopedia of Chemical Technology,* 3rd edition, vol. 5, pp 344–345, J. Wiley 1979.)

In detail, the method of the invention can be carried out as follows:

The lipases used correspond to the designations given above, as do the proteases.

Liming method

In a hair jellification method, the enzymes or enzyme combinations are added to the soaked hides or skins at the beginning of the process. Enzyme combinations EC having the following composition have proved particularly useful:

| | |
|---|---|
| 100–1,000 KLVU | alkaline bacterial protease, e.g. from *B. subtilis, B. licheniformus* |
| 0.1–5 wt. % | lipase having an activity of 5,000 LVU/mg |
| 1.0–20 wt. % | Na tripolyphosphate |
| to 100 wt. % | Na sulfate. |

The product is conventionally dosed in the range from 0.05–1 percent by weight of the salted or green hides.

As a guide value for the float length, 150±50 percent is given; the temperature is preferably at 28 C°. Although sulfur liming is involved, the liming bath contains relatively small amounts of the liming chemicals, typically sodium hydrosulfide (72 %)—as a guide value about 0.6 percent by weight—and sodium sulfide (60 %)—as a guide value about 0.2 percent by weight—, as well as hydrated lime—guide value about 1.5 percent by weight—based on the hides, at a pH value of 12.8.

The batch is agitated for about 1½ hours under these conditions before the enzymes, particularly the enzyme combination EC II is added—as a guide value in amounts of about 0.3 percent by weight—preferably with about the same amount of hydrated lime as is already present, and is constantly agitated for a short time at first, and then left to react over a longer period of time, for example about 16 hours, with occasional stirring.

After draining off the float and washing, preferably with about 150 percent of water at 28 C°, unhaired hides of good quality are obtained. The smoothness and the freedom from scud of the unhaired hides are emphasized.

In a liming process in which hair is retained, the hides or skins are soaked as usual. It was found that hides and skins which have been pretreated or soaked with an alkaline protease at pH 8–11 for 4–20 hours and then are treated at the same pH for 2–6 hours with an alkaline lipase in the same bath, or in a new bath, are outstandingly prepared for a subsequent proteolytic unhairing. Advantageously, a hair immunization step directly follows the soak in which—following DE-A 38 02 640 corresponding to U.S. Pat. No. 4,960,428 granted Oct. 2, 1990 —hydrated lime and organic thio compounds together with amines in about 80 percent of water at about pH 12 can be used. Then, a hair loosening step usually follows. When the enzyme combination EC-II to be added according to the invention is used, a sharply reduced amount of sulfide is sufficient, for example 0.4 percent by weight of sodium hydrosulfide (72%), based on the hides. After a relatively short time, for example about 2 hours, the hides are free of hair. Suitably, about 70 percent by weight of water are added together with about 2 percent by weight of hydrated lime and about 0.3 percent by weight of sodium hydroxide solution (50%) and the process is continued over a certain period of time, suitably about 14 hours at 28 C° with short periods of agitation at moderate intervals. Subsequently the float is drained off and further working up is continued in the manner usually followed by the industry. Usually, the liming procedure can directly follow fleshing and splitting of the hides.

Bating

The hide material prepared in the usual way, e.g. fleshed and split unhaired hides, are washed and delimed (supra.). Generally, the addition to a float of about 50 percent and at 30 C° of about 2 percent by weight, based on the hide material, of a deliming agent is sufficient, for example in the form of the above-mentioned acids (e.g. carbon dioxide or dicarboxylic acids in combination with ammonium salts), which suitably are added in two portions each of 1 percent by weight and are each allowed to act for 10 or 20 minutes, whereby the pH decreases into the region of about 8.5. For the bate itself, as a rule about the same amount of water is added, preferably at 35 C°, and the enzyme is added, preferably as enzyme combination EC.

As a rule, enzyme combinations EC of the following typical composition are used:

| | |
|---|---|
| 50–100 KLVU | pancreatic complex |
| 0.5–5 wt. % | alkaline lipase having an activity of 5000 LU/mg |
| 1.0–30 wt. % | Sodium tripolyphosphate |
| to 100 wt. % | Sodium sulfate or ammonium sulfate. |

After deliming, the product according to the invention is added at 30°–35 ° C. over 20–120 minutes in an amount of 0.5–2 percent by weight of the unhaired hides.

Suitably, the batch is agitated for about 1 hour at 33 C° with the pH at about 8–8.5, a guide value is 7.9. Then the float is drained off and the batch is washed, with agitation, with about 200 percent of water at about 22 C°. In the fashion conventional in tanneries, pickling and chrome tanning can then follow.

Advantageous effects

The methods according to the invention are based on the observation that enzyme preparations which contain one or more lipases whose activity optimum, depending on manufacture, is in the pH range of 10–11, can be used with outstanding success both under the conditions of liming at a pH of about 13 and in bating in the pH region of 7–9. The effect in combination with corresponding neutral and alkaline proteases is particularly pronounced, as summarized by the phrases:

- improved loosening of pigment scud
- improved degreasing of the unhaired hides
- fewer grain wrinkles and grain damage
- performance of a sulfide-free and also a sulfide-poor unhairing which retains the hair.

With the use of the alkaline lipases in the bate at pH 7–9, preferably in combination with pancreatic enzymes, an improved loosening of scud is observed.

The following examples serve to illustrate the invention:

EXAMPLES

Products Used:

Product EC-I: Bating agent containing lipase

| | |
|---|---|
| 100 KLVU | pancreatic enzyme complex |
| 1 wt .% | alkaline lipase "LIPOLASE ™ 100 T", obtained by cloning the gene from *Humicola lanuginosa* and expressing this gene in *Aspergillus oryzae* Novo), 5,000 LU/mg |
| 15 wt. % | sodium tripolyphosphate |
| 20 wt. % | sodium sulfate |
| to 100 wt. % | ammonium sulfate. |

Product EC-II: Liming agent containing lipase

| | |
|---|---|
| 500 KLVU | alkaline bacterial protease from *Bacillus subtilis* |
| 2 wt. % | alkaline lipase "LIPOLASE ™ 100 T" obtained by cloning the gene from *Humicola lanuginosa* and expressing this gene in *Aspergillus oryzae* |
| to 100 wt. % | sodium sulfate |

Deliming agent: Ammonium sulfate/dicarboxylic acid basis

Emulsifier combination ES:

| | |
|---|---|
| 15 wt. % | $C_{13}$-fatty alcohol ethoxylate with 8 mols of ethylene oxide |
| 15 wt. % | $C_{15}$-paraffin sulfonate, sodium salt |
| 6 wt % | $C_{16}$–$C_{18}$-fatty amino ethoxylate with 6 mols of ethylene oxide, quaternized |
| to 100 wt. % | water. |

Test 1: Preparation of soft shoe-upper leather - bating

Material:

| | |
|---|---|
| Split unhaired cowhide (2.5 mm). | (Directions based on the weight of the unhaired hides) |
| Starting material: | 100 kg of skin material |

Washing:

| | |
|---|---|
| 200% | water, 30 C°, agitate for 10 minutes. drain float. |

-continued

| Test 1: Preparation of soft shoe-upper leather - bating | |
|---|---|
| Deliming: | |
| 50% | water at 30 C° |
| 1% | deliming agent, agitate for 10 minutes |
| +1% | deliming agent, agitate for 20 minutes<br>K = pH 8.5, colorless |
| Bate: | |
| +50% | water, 35 C° |
| 1% | product EC-I<br>agitate every 60 minutes, pH 8.3, 33 C° drain off float |
| Washing: | |
| 200% | water, 22 C°, agitate for 10 minutes<br>drain float |
| Pickling, Chrome Tanning:<br>As usual in the tannery. | |
| Analytical Data: | |
| Fat content in the float: | 0.6 g/l |
| Fat content in the unhaired hide: | 0.25%, based on dry weight. |
| For comparison, a test was carried out with the same product as product EC-I, but without lipase: | |
| Fat content in the float: | 0.4 g/l |
| Fat content in the unhaired hide: | 0.4%, based on dry weight. |

| Test 2: Preparation of garment leather (sheepskin) bate<br>(Directions based on weight of unhaired skins) | |
|---|---|
| Starting material:<br>100 kg unsplit unhaired sheepskins<br>Tanning vat | |
| Washing: | |
| 200% | water, 30 C°<br>agitate for 10 minutes<br>drain off float. |
| Deliming: | |
| 50.0% | water, 30 C°, agitate |
| 1.4% | deliming agent, agitate for 20 minutes, pH 8.6 |
| Bate: | |
| +50.0% | water, 35 C° |
| 0.3% | emulsifier ES |
| 1/0% | product EC-I<br>agitate for 2 hours<br>pH 8.5, 32 C°<br>drain off float. |
| Washing: | |
| 200.0% | water, 22 C°<br>run for 10 minutes<br>drain off float. |
| Pickling/tanning:<br>as usual in the tannery. | |
| Analytical data: | |
| Fat content: | |
| Float | 9.8 g/l |
| Unhaired hide | 3.5%, based on dry weight. |
| Product EC-I, but without alkaline lipase, was tested in the same way: | |
| Fat content: | |
| Float | 6.1 g/l |
| Unhaired hide | 4.9%, based on dry weight. |

| Test 3: Preparation of garment leather (pigskin), bate | |
|---|---|
| Material:<br>Pigskins split to 2.0 mm<br>Tanning vat<br>(Directions based on weight of unhaired skins) | |
| Washing: | |
| 200% | water, 30 C°; 10 minutes; drain off float |
| Deliming: | |
| 50% | water, 30 C° |
| 2% | deliming agent<br>agitate for 30 minutes<br>float, pH 8.6 |
| Bate: | |
| +100.0% | water, 35 C° |
| 0.3% | emulsifier combination ES |
| 1.0% | product EC-I<br>agitate for 90 minutes<br>pH = 8.3; temperature 33 C°. |
| Washing: | |
| 200% | water; 22 C°<br>agitate for 10 minutes<br>drain off float |
| Pickle/Chrome tanning:<br>as usual in the tannery. | |
| Analytical data: | |
| Fat content | |
| Float | 13.1 g/l |
| Unhaired hides | 7.1%, based on dry weight. |
| For comparison, product EC-I, without alkaline lipase, was used in the same working method: | |
| Fat content: | |
| Float | 10.2 g/l |
| Unhaired hides | 8.9% based on dry weight. |

| Test 4: Enzymatic unhairing of sheepskins | |
|---|---|
| Material: | |
| 200.0% | water, 28 C° |
| 0.1% | nonionic emulsifier, comprising $C_{13}$-alcohol with 8 mols ethylene oxide<br>agitate for 20 minutes<br>let stand for 30 minutes<br>agitate for 20 minutes<br>drain off float |
| Main soak: | |
| 200.0% | water, 26 C° |
| 0.2% | enzymatic soaking agent comprising proteolytic enzyme from *Bacillus licheniformis*; 4000 LVU/g |
| 0.7% | pH 9–10<br>agitate for 260 minutes<br>drain off float |
| Unhairing: | |
| 200% | water, 32 C° |
| 0.005% | lipase, alkaline having 5000 LVU/mg |
| 0.6–1.1% | soda, pH 8–10<br>agitate 3–4 hours |
| +2% | proteolytic unhairing enzyme from *Aspergillus parasiticus*, 4000 LVU/g<br>agitate for 60 minutes<br>then agitate for 1 minute per hour for a further 16–24 hours;<br>pH = 9.1<br>temperature = 28 C°<br>drain off float<br>unhair |

-continued

| Test 4: Enzymatic unhairing of sheepskins | |
|---|---|
| Washing: | |
| 200% | water; 26 C° |
| | agitate 10 minutes |
| | drain off float |
| | conventional opening of the hide structure with hydrated lime treatment for 4–8 hours |

| Test 5: Liming (sulfide-poor) of salted cowhides of weight class 30–39 for the preparation of furniture leather | |
|---|---|
| Tanning vat: Presoak: | |
| 150% | water, 26 C° |
| | agitate for 30 minutes |
| | let stand for 30 minutes |
| | drain off float |
| Soak: | |
| 150.0% | water, 26 C° |
| 0.3% | nonionic surfactant |
| 0.25% | proteolytic enzyme product from *Bacillus subtilis*; 4400 LVU/g |
| | sodium hydroxide solution (33%) |
| | pH 9.5–10 |
| | agitate for 6 |
| | drain float |
| Liming: | |
| 150.0% | water, 28 C° |
| 0.6% | sodium hydrosulfide (72%) |
| 0.2% | sodium sulfide (60%) |
| 1.5% | hydrated lime; pH 12.8 |
| | agitate 90 minutes |
| +0.3% | test product EC-II |
| 1.5% | hydrated lime |
| | agitate 30 minutes, then for 2 minutes per hour for a further 16 hours |
| | drain off float |
| Washing: | |
| 150.0% | water, 28 C° |
| | agitate 10 minutes |
| | drain off float |
| The unhaired hides are very smooth and free of scud. | |

| Test 6: Hair-retaining liming of salted cowhides, weight class 30–39, for preparation of furniture leather | |
|---|---|
| Tanning vat: Presoak: | |
| 150.0% | water, 26 C° |
| 0.1% | nonionic surfactant comprising tallow ethoxylate |
| | 2 hours (let rest 30 minutes, agitate 30 minutes) |

-continued

| Test 6: Hair-retaining liming of salted cowhides, weight class 30–39, for preparation of furniture leather | |
|---|---|
| Soak: | |
| 150.0% | water, 28 C° |
| 0.2% | nonionic surfactant comprising fatty alcohol ethoxylate |
| 0.25% | proteolytic enzyme product from *Bacillus subtilis*, 4400 LVU/g |
| | bring to pH 9.5–10 with lye (33%) |
| | agitate for 5 hours |
| | drain off float |
| Immunization: | |
| 80.0% | water, 28 C° |
| 1.5% | liming auxiliary comprising alkanolamine and organic thio compounds |
| 1.2% | hydrated lime |
| | agitate 60 minutes |
| +0.6% | sodium hydrosulfide, 72% |
| 0.3% | test product EC-II |
| | after 2 hours the hides are free of hair |
| +70.0% | water, 28 C° |
| 2.0% | hydrated lime |
| 0.3% | sodium hydroxide solution (50%) |
| | agitate for 2 minutes per hour for 14 hours |
| | drain off float |
| | work up further as usual in the tannery |

Treatment with the enzyme product according to the invention permits omitting a post-liming. Opening of the hide structure is optimum after a processing time of 16–18 hours.

We claim:

1. A method for preparing unhaired hides or skins ready for tanning which comprises liming unhaired hides or skins in a pH region from 11.5–14 in a float comprising an amount, sufficient for liming, of a 1,3-specific recombinant alkaline lipase having an activity optimum in the pH range from 9–11, a molecular weight as determined by SDS-PAGE of about 35 kD and a pI of about 4.4; wherein said recombinant alkaline lipase degreases said hides or skins; said recombinant alkaline lipase having been obtained by cloning a non-recombinant alkaline lipase gene from *Humicola lanuginosa* into *Aspergillus oryzae* and using said *Aspergillus oryzae* to produce said recombinant alkaline lipase.

2. The method as in claim 1 wherein the recombinant alkaline lipase is added concurrently with an amount, sufficient for liming, of an alkaline protease.

3. The method as in claim 1 wherein the hides or skins are limed in a pH range from 12–13.5.

4. The method as in claim 1 wherein the float additionally contains a sequestering agent to avoid calcium soaps.

5. The method as in claim 1 wherein the float is from 50 to 250 percent by weight of the hides or skins.

6. The method as in claim 5 wherein the float is 150±50 percent by weight of the hides or skins.

* * * * *